United States Patent [19]

Cooper et al.

[11] Patent Number: 5,716,619
[45] Date of Patent: Feb. 10, 1998

[54] TREATMENT OF TYPE 2 DIABETES MELLITUS

[75] Inventors: Garth J.S. Cooper, Woodstock, England; Howard Greene, Jr., Rancho Santa Fe, Calif.

[73] Assignee: Amylin Pharmaceuticals, Inc., San Diego, Calif.

[21] Appl. No.: 295,361

[22] Filed: Aug. 23, 1994

Related U.S. Application Data

[63] Continuation of Ser. No. 901,338, Jun. 19, 1992, abandoned, which is a continuation of Ser. No. 715,302, Jun. 4, 1991, Pat. No. 5,266,561, which is a continuation of Ser. No. 275,475, Nov. 23, 1988, abandoned, which is a continuation-in-part of Ser. No. 142,447, Jan. 11, 1988, abandoned.

[51] Int. Cl.$^6$ .................. A61K 39/395; A61K 38/00
[52] U.S. Cl. .................. 424/130.1; 424/131.1; 424/139.1; 424/141.1; 424/145.1; 424/156.1; 514/12; 514/866
[58] Field of Search .................. 424/130.1, 131.1, 424/139.1, 141.1, 145.1, 156.1; 514/12, 866

[56] References Cited

U.S. PATENT DOCUMENTS

| | | |
|---|---|---|
| 4,530,839 | 7/1985 | Evans . |
| 4,661,586 | 4/1987 | Levy et al. ..................... 530/387 |
| 4,687,839 | 8/1987 | Kempe . |
| 4,697,002 | 9/1987 | Kempe . |
| 4,720,483 | 1/1988 | Janz . |
| 4,736,023 | 4/1988 | Evans . |
| 5,266,561 | 11/1993 | Cooper et al. ..................... 514/12 |

FOREIGN PATENT DOCUMENTS

| | | |
|---|---|---|
| 156772 | 10/1985 | European Pat. Off. . |
| 188400 | 7/1986 | European Pat. Off. . |
| 263802 | 4/1988 | European Pat. Off. . |
| 270376 | 6/1988 | European Pat. Off. . |
| 2141430 | 12/1984 | United Kingdom . |
| 8501658 | 4/1985 | WIPO . |

OTHER PUBLICATIONS

Foord et al., Eur. J. Biochem. 170:373 (1987).
Sewell et al., Soc. Neurosci. Abs. 13:42 (1987).
Kimura et al., Neuropeptides 9:75 (1987).
Minvielle et al., FEBS Lett. 203:7 (1986).
Morris et al., Nature 308:746 (1984).
Craig et al., Biochem. Soc. Symp. 52:91 (1986).
Tippins et al., J. Hypertens., 4:S102 (1986).
Tippins et al., Biochem. Biophys. Res. Commun., 134:1306 (1981).
Holman et al., Peptides, 7:231 (1986).
Lenz et al., Gut, 26:550 (1985).
Westermark et al., Biochem. Biophys. Res. Commun. 140:827 (1986).
Westermark et al., Diabetologia, 30:887 (1987).
Westermark, et al., Proc. Nat. Acad. Sci. (USA), 84:3881 (1987).
Westermark et al., Am. J. Pathol., 127:414 (1987).
Cooper et al., Proc. Nat. Acad. Sci. (USA) 84:8628 (1987).
Cooper et al., Lancet 2:966 (1987).
Goding (1983) "Monoclonal Antibodies," Academic Press, Inc., Orlando, pp. 56–97.
Koike et al (1987) Diabetes 36:539–541.
Gregonadis et al (1993) Trends in Biotech. 11:440–442.
Leighton et al (1987) Nature 335:632–635.

*Primary Examiner*—Paula K. Hutzell
*Assistant Examiner*—Benet Prickril
*Attorney, Agent, or Firm*—Lyon & Lyon LLP

[57] ABSTRACT

Antibody methods for blocking the effects of diabetes-associated peptide, or "amylin", a hormone found in the amyloid masses of Type 2 diabetics, are disclosed. This putative hormone has been discovered to function both to inhibit insulin secretion and to inhibit glycogen synthesis. Regulation is accomplished by blocking the binding of amylin or amylin agonists, including calcitonin gene related peptide (CGRP), or biologically active sub-peptides thereof. Inhibitors include antibodies directed to amylin and amylin agonist active sites. Other antagonists include anti-idiotype antibodies directed to antibodies directed to amylin.

8 Claims, No Drawings

TREATMENT OF TYPE 2 DIABETES MELLITUS

This application is a continuation of application Ser. No. 07/901,338, filed Jun. 19, 1992 now abandoned, which is a continuation of application Ser. No. 07/715,302, filed Jun. 4, 1991, now U.S. Pat. No. 5,266,561, which is a continuation of application Ser. No. 07/275,475, filed Nov. 23, 1988, now abandoned, which is a continuation-in-part of application Ser. No. 07/142,447 filed Jan. 11, 1988, now abandoned.

BACKGROUND

1. Field of the Invention

The field of the invention is medicine and, more particularly, the treatment of non-insulin-dependent, or Type 2, diabetes mellitus.

2. Description of Related Art and Introduction to the Invention

Diabetes mellitus is the most common of the serious metabolic diseases affecting humans. It may be defined as a state of chronic hyperglycemia, i.e., excess sugar in the blood, consequent upon a relative or absolute lack of insulin action. Insulin is a peptide hormone produced and secreted by B cells within the islets of Langerhans in the pancreas. Insulin promotes glucose utilization, protein synthesis, and the formation and storage of neutral lipids. It is generally required for the entry of glucose into muscle. Glucose, or "blood sugar", is normally present in humans at concentrations of about 0.8–1.2 grams (4.0–7.0 millimoles) per liter and is the principal source of carbohydrate energy for man and many other organisms. Excess glucose is stored in the body (especially in the liver and muscles) as glycogen, a starch-like substance which is, essentially, polymerized glucose. Glycogen is metabolized into glucose as needed to meet bodily requirements.

Glucose normally stimulates both the secretion and biosynthesis of insulin. In addition, to this glucose-stimulated insulin secretion, however, there exists a basal insulin secretion, the biological process by which insulin is released into the circulation in the absence of stimulation by levels of glucose, or other agents that promote insulin secretion, elevated above their "fasting" or non-fed levels. The normal basal (or fasting) level of insulin is usually about 10–16 µU/ml (or 440–700 pmol/L), which occurs during normal fasting glucose levels of about 4.0 to 5.5 mmol/L. Levels of insulin secretion stimulated by glucose amounts elevated above the normal fasting level of glucose can reach or exceed 320 µU/ml (or 14 nmol/L) in non-diabetics.

Glycogen is normally synthesized from glucose at a basal rate, i.e., the rate of synthesis that proceeds in the absence of glucose-stimulated insulin secretion. At the normal basal rate of insulin secretion, in fact, about 90 percent of total glycogen synthesis is probably not directly stimulated by insulin. Of course, insulin-stimulated glycogen synthesis is a normal occurrence and, at the maximal glucose-stimulated insulin secretion rate, approximately seventy percent of total glycogen synthesis is caused by direct insulin stimulation.

The hyperglycemia associated with diabetes mellitus is a consequence of both the underutilization of glucose and the overproduction of glucose from protein due to relatively depressed or nonexistent levels of insulin. In so-called Type 2 diabetics, for example, maximally glucose-stimulated insulin levels typically fail to rise above 90 µU/ml (4.0 nmol/L).

Not only is diabetes mellitus characterized by a series of hormone induced metabolic abnormalities, but also by long term complications involving the eyes, nerves, kidneys and blood vessels, and by a lesion involving thickening of the cellular basement membranes. These diabetic complications include premature atherosclerosis, intercapillary glomerulosclerosis, retinopathy, and neuropathy. The major cause of death and disability in diabetes is coronary artery disease. Garcia M. J., McNamara P. M., Gordon T., Kannell W. E., *Morbidity and mortality in diabetics in the Framingham population. Sixteen year follow-up.* Diabetes 1974; 34:105–111. This publication and all other references noted herein are hereby incorporated by reference.

Although the diagnosis of symptomatic diabetes mellitus is not difficult, detection of asymptomatic disease can raise a number of problems. Diagnosis may usually be confirmed by the demonstration of fasting hyperglycemia. In borderline cases, the well-known glucose tolerance test is usually applied. Some evidence suggests, however, that the oral glucose tolerance test over-diagnoses diabetes to a considerable degree, probably because stress from a variety of sources (mediated through the release of the hormone epinephrine) can cause an abnormal response. In order to clarify these difficulties, the National Diabetes Data Group of the National Institutes of Health have recommended criteria for the diagnosis of diabetes following a challenge with oral glucose. National Diabetes Data Group: *Classification and diagnosis of diabetes mellitus and other categories of glucose intolerance.* Diabetes 1979; 28:1039.

The frequency of diabetes mellitus in the general population is difficult to ascertain with certainty, but the disorder is believed to affect more than ten million Americans. Diabetes mellitus generally cannot be cured but only controlled. In recent years it has become apparent that there are a series of different syndromes included under the umbrella term "diabetes mellitus". These syndromes differ both in clinical manifestations and in their pattern of inheritance. The term diabetes mellitus is considered to apply to a series of hyperglycemic states which exhibit the characteristics noted above.

Diabetes mellitus has been classified into two basic categories, primary and secondary, and includes impaired glucose tolerance, which may be defined as a state associated with abnormally elevated blood glucose levels after an oral glucose load, in which the degree of elevation is insufficient to allow a diagnosis of diabetes to be made. Persons in this category are at increased risk for the development of fasting hyperglycemia or symptomatic diabetes relative to persons with normal glucose tolerance, although such a progression cannot be predicted in individual patients. In fact, several large studies suggest that most patients with impaired glucose tolerance (approximately 75 percent) never develop diabetes. See Jarrett R. J., Keen H., Fuller J. H., McCartney M., *Worsening to diabetes in men with impaired glucose tolerance ("Borderline diabetes").* Diabetologia 1979; 16:25–30.

Primary diabetes mellitus includes:
1. Insulin-dependent diabetes mellitus (IDDM, or Type 1)
2. Non-insulin-dependent diabetes mellitus (NIDDM, or Type 2)
   a. Non-obese Type 2
   b. Obese Type 2
   c. Maturity-onset diabetes of the young (MODY).

Secondary diabetes mellitus includes diabetes mellitus secondary to:
1. Pancreatic disease
2. Hormonal abnormalities other than primary lack of insulin action (e.g., Cushings disease, Acromegaly, Phaeochromacytoma)

3. Drug or chemical induction
4. Insulin receptor abnormalities
5. Genetic syndromes
6. Other.

It should be noted that the category of secondary diabetes mellitus is of markedly less importance than is that of primary diabetes mellitus in terms of the absolute numbers of individuals affected, at least in the western world. Also, the appearance of abnormal carbohydrate metabolism in association with any of the above secondary causes does not necessarily indicate the presence of underlying diabetes although in many cases a mild asymptomatic, primary diabetes may be made overt by the secondary illness.

Type 2 or non-insulin-dependent diabetes is of present concern herein. Insulin resistance is a characteristic of Type 2 diabetes and may be defined as a failure of the normal metabolic response of peripheral tissues to the action of insulin. In other words, it is a condition where the presence of insulin produces a subnormal biological response. In clinical terms, insulin resistance is present when normal or elevated blood glucose levels persist in the face of normal or elevated levels of insulin. It represents, in essence, a glycogen synthesis inhibition, by which either basal or insulin-stimulated glycogen synthesis, or both, are reduced below normal levels. Insulin resistance plays a major role in Type 2, as demonstrated by the fact that the hyperglycemia present in Type 2 diabetes can sometimes be reversed by diet or weight loss sufficient, apparently, to restore the sensitivity of peripheral tissues to insulin. There are at least two causes of hyperglycemia in Type 2 diabetes.

1. Failure of glucose storage to be activated

It is known that the storage of carbohydrate as glycogen is a likely consequence of intermittent carbohydrate feeding because each calorie load can easily exceed immediate metabolic needs. In the short term, storage provides a means of clearing the plasma of glucose. Recent data have suggested that the site of immediate glucose disposal is skeletal muscle. See Katz L. D., Glickman M. G., Rapoport S., Ferrannini E., De Fronzo R. A., *Splanchnic and peripheral disposal of oral glucose in man*. Diabetes 1983; 32:675. The failure of glucose storage to be activated in Type 2 diabetics during the administration of carbohydrate leads to reduced tissue uptake of glucose and may be a major defect leading to insulin resistance. See Lillioja S., Mort D. M., Zawadzki J. K., Young A. A., Abbott W. G., Bogardus C., *Glucose storage is a major determinant of in Vivo "insulin resistance" in subjects with normal glucose tolerance*. J Clin Endoc Metab 1986; 62:922–927.

2. Defect in insulin release

However, a defect in insulin storage or release is also involved, because massively obese people with marked insulin resistance usually do not have hyperglycemia or diabetes mellitus. See Wajngot A., Roovete A. et al., *Insulin resistance and decreased insulin response to glucose in lean Type 2 diabetics*. Proc Natl Acad Sci USA 1982; 79:4432–4436. This finding suggests that the normal pancreas has sufficient reserve to compensate for insulin resistance imposed by obesity or other factors while the pancreas in Type 2 subjects does not. In this sense, therefore, the primary defect can be considered to be a dysfunctional islet B-cell, although the abnormality would not be recognized without the additional symptom of insulin-resistance. It may be that those patients with non-obese Type 2 have a more severe defect in insulin release.

The nature of the islet B-cell lesion in Type 2 diabetes is unclear. Unlike those in Type 1 diabetes, the Type 2 B-cells retain the ability to synthesize and secrete insulin, as evidenced by the presence of insulin and C-peptide both in these cells and circulating in the plasma. Available studies suggest that there is a modest reduction in the numbers of B-cells, but this is insufficient to account for the observed reduction in insulin secretion. See Stefan Y., Orci L., et al., Diabetes 1982; 31:694–700. It has therefore been thought to be likely that the remaining B-cells have impaired function, manifested as a delay in the initial secretion of insulin in response to a glucose load, even in the earliest detectable stage of the disease, and by the fact that in Type 2 diabetics, less insulin is secreted at any glucose concentration in both overtly diabetic subjects and in those with clinically latent forms of the disease.

The primary aim of treatment in all forms of diabetes mellitus is the same, namely the reduction of blood glucose levels to as near normal as possible, thereby minimizing both the short- and long-term complications of the disease. See Tchobroutsky G., *Relation of diabetic control to development of microvascular complications*. Diabetologia 1978; 15:143–152.

The treatment of Type 1 diabetes necessarily involves the administration of replacement doses of insulin, administered by the parenteral route. In combination with the correct diet and self-blood glucose monitoring, the majority of Type 1 patients can achieve reasonable control of blood glucose. Treatment of Type 2, in contrast to the treatment of Type 1 frequently does not require the use of insulin. Therapy may be based on diet and lifestyle changes, augmented by therapy with oral hypoglycemic agents (sulfonylureas or biguanides).

Modification of the diet and lifestyle is the first line of therapy in Type 2. If obesity is present, it is also necessary to reduce body weight to near-ideal levels. Important features of the diabetic diet include an adequate but not excessive total calorie intake, with regular meals; restriction of the content of saturated fat; a concomitant increase in the polyunsaturated fatty acid content; and, an increased intake of bound carbohydrate ("dietary fiber"). A second important lifestyle modification is the maintenance of regular exercise, as an aid both to weight control and also to reduce the degree of insulin resistance.

Thus, institution of therapy in Type 2 usually involves a trial of dietary therapy, typically for six to twelve weeks in the first instance. If after an adequate trial of diet and lifestyle modification, fasting hyperglycemia persists, then a diagnosis of "primary diet failure" may be made, and either a trial of oral hypoglycemic therapy or direct institution of insulin therapy will be required to produce blood-glucose control and, thereby, to minimize the complications of the disease. It must be noted that although weight loss is the aim of lifestyle and dietary modification, it is, of course, frequently not achieved.

Type 2 diabetics that fail to respond to diet and weight loss may respond to therapy with sulfonylureas. The class of sulfonylurea drugs includes Acetohexamide, Chlorpropamide, Tolazamide, Tolbutamide, Glibenclaminde, Glibornuride, Gliclazide, Glipizide, Gliquidone and Glymidine. These drugs act primarily by augmenting residual pancreatic beta-cell function and are relatively easy to use. It is important to understand, however, that all sulfonylureas may lead to hypoglycemic reactions, including coma, four or more hours after meals. Indeed, hypoglycemic episodes may last for several days so that prolonged or repeated glucose administration is required. Reactions have occurred after one dose, after several days of treatment, or after months of drug administration. Most reactions are observed in patients over 50 years of age, and they are more likely to occur in patients with impaired hepatic or renal function. Over-dosage, or inadequate or irregular food intake may initiate hypoglycemia. Other drugs can increase the risk of hypoglycemia from sulfonylureas including other hypoglycemic agents, sulfonamides, propranolol, salicylates, phenylbutzone, probenecid, dicumarol, choloramphenicol, monoamine oxidase inhibitors, and alcohol.

Additionally, it is understood that sulfonylureas should not be used in patients with hepatic or renal insufficiency because of the importance of the role of the liver in their metabolism and the kidney in the excretion of the drugs and their metabolites. Furthermore, these compounds are best avoided in obese patients unless their symptoms and diabetic control have not improved despite weight loss to within 15 percent of their ideal body weight, as they tend to encourage weight gain.

The suggestion has also been made that sulfonylureas may cause an increase in morbidity and mortality from coronary artery disease. See University Group Diabetic Programme. *A study of the effects of hypoglycemic agents on vascular complications in patients with adult-onset diabetes*. Diabetes 1976; 25:1120–1153. That study has been criticized for analyzing data according to the treatment groups to which patients were assigned, regardless of adherence to therapy. Critics have suggested that patients given insulin in variable dosage to optimize glucose control might have had a decrease in cardiovascular mortality (see Kilo C., Williamson J. R., Choi S. C., Miller J. P., *Refuting the University Group Diabetic Programme conclusion that insulin treatment does not prevent vascular complications in diabetes*. Adv Exp Med Biol 1979; 119:307–311), and that the drug Tolbutamide might only be associated with increased mortality if the fasting blood glucose remains above 11.1 mmol/L. See Kilo C., Miller J. P., Williamson J. R., *The crux of the university group diabetic programme. Spurious results and biologically inappropriate data analysis*. Diabetologia 1980; 19:179–185. Nevertheless, and in spite of the availability of therapy with oral agents, the rate of morbidity and mortality from coronary artery disease in Type 2 populations remains considerably higher than that in non-diabetics.

Another group of compounds, the biguanides, was developed independently of the sulfonylureas. Of the three antidiabetic biguanides, which include phenformin, only metformin is useful in treating Type 2 diabetes with a lesser risk of side-effects when applied in a well controlled regimen. See Schafer G., *Biguanides. A review of history, pharmacodynamics and therapy*. Diabetes et metabolism 1983; 9:148–163. Metformin does not cause an increase in insulin secretion, but is thought to exert its hypoglycemic effect mainly by increasing peripheral glucose utilization. Like the sulfonylureas, however, it is only effective in diabetics with a degree of residual endogenous insulin secretion and, therefore, it presumably acts by increasing the sensitivity of peripheral tissues to insulin. Other metabolic effects of metformin which are believed to contribute to its antidiabetic action include: 1) the induction of intestinal malabsorption of glucose and other nutrients; 2) the inhibition of increased hepatic and renal gluconeogenesis; and 3) the inhibition of lipolysis and free fatty acid oxidation. Unlike insulin, however, metformin does not encourage lipo-genesis. It is most frequently used in overweight diabetics who cannot, or will not, lose weight. Metformin does not exert a hypoglycemic action in non-diabetic subjects.

Because of the real and unpredictable risk of the frequently fatal complication of lactic acidoses, use of the biguanide phenformin has been discontinued. Metformin is not free from this hazard, however, and the decision to use it in therapy must therefore be taken with care, and only in those patients who have undergone primary dietary failure, and who either are overweight or have also undergone "secondary sulfonylurea failure" (and are overweight). It is recommended that metformin not be given to patients with renal disease or a history of alcohol abuse, and its use must immediately be stopped if nausea, vomiting, diarrhea or any intercurrent illness appears.

It is noteworthy that, notwithstanding the above-noted avenues of treatment, insulin therapy remains the treatment of choice for many patients with Type 2 diabetes, especially those who have undergone primary diet failure and are not obese, or those who have undergone both primary diet failure and secondary oral hypoglycemic failure. But it is equally clear that insulin therapy must be combined with a continued effort at dietary control and lifestyle modification, and in no way can be thought of as a substitute for these. In order to achieve optimal results, insulin therapy should be followed with self-blood glucose monitoring and appropriate estimates of glycosylated blood proteins. Insulin may be administered in various regimens alone, two or multiple injections of short, intermediate or long acting insulins, or mixtures of more than one type. The best regimen for any patient must be determined by a process of tailoring the insulin therapy to the individual patient's monitored response.

The trend to the use of insulin therapy in Type 2 diabetes has increased with the modern realization of the importance of strict glycemic control in the avoidance of long-term diabetic complications. In non-obese Type 2 diabetics with secondary oral hypoglycemic failure, however, although insulin therapy may be successful in producing adequate control, a good response is by no means assured. See, e.g., Rendell M., Slavin D., Meltz G., Simpson J., Barquet A., *A case of maturity-onset diabetes mellitus resistant to insulin but responsive to Tolbutamide*. Ann Int Med 1979; 90:195–97. In one study, only 31 percent of 58 non-obese patients who were poorly controlled on maximal doses of oral hypoglycemic agents achieved objectively verifiable improvement in control on a simple insulin regimen. See Peacock I., Tattersall R. B., *The difficult choice of treatment for poorly controlled maturity-onset diabetes: tablets or insulin*. Br Med J 1984; 288:1958–1959. In obese diabetics with secondary failure, the picture is even less clear-cut because in this situation insulin frequently increases body weight, often with a concomitant deterioration in control.

It will be apparent, therefore, that the current state of knowledge and practice with respect to the therapy of Type 2 diabetes is by no means satisfactory. The majority of patients undergo primary dietary failure with time, and the majority of obese Type 2 diabetics fail to achieve ideal body weight. Although oral hypoglycemic agents are frequently successful in reducing the degree of glycemia in the event of primary dietary failure, many authorities doubt that the degree of glycemic control attained is sufficient to avoid the occurrence of the long term complications of atheromatous disease, neuropathy, nephropathy, retinopathy and peripheral vascular disease associated with longstanding Type 2 diabetes. The reason for this can be appreciated in the light of the current realization that even minimal glucose intolerance, approximately equivalent to a fasting plasma glucose of 5.5 to 6.0 mmol/L, is associated with an increased risk of cardiovascular mortality. See Fuller J. H., Shipley M. J., Rose G., Jarrett R. J., Keen H., *Coronary heart disease risk and impaired glucose tolerance*. The Whitehall study. Lancet 1980; 1:1373–1378. It is also not clear that insulin therapy produces any improvement in long-term outcome over treatment with oral hypoglycemic agents. Thus, it can be appreciated that a superior method of treatment would be of great utility. Such a method, and compounds useful therefor, are described and claimed herein.

SUMMARY OF THE INVENTION

The invention provides compounds and methods for regulation of the effects of amylin, a hormone isolated from the pancreatic amyloid masses typically found in Type 2 diabetics and which we have found leads in elevated amounts to abnormal insulin release and abnormal glycogen synthesis. This regulation can be accomplished, or example, by blocking the binding of amylin and/or calcitonin gene related peptide (CGRP) and/or other amylin agonists, or biologically active sub-peptides of amylin or CGRP, by the use of competitive inhibitors including substituted or altered peptides or subpeptides of amylin or CGRP, or by the regulation of the expression or production or release of amylin or CGRP, or active sub-peptides thereof.

Chemical antagonists to amylin which bind to the amylin receptor without triggering a full amylin response are used to reduce the effects of amylin or amylin agonists (including CGRP) or biologically active subpeptides thereof which act to inhibit the body's basal and insulin-stimulated responses to glucose, or to prevent the interference of those molecules with insulin release. Thus, unamidated amylin, the substituted $ser^2$, $ser^7$ peptides and subpeptides of amylin and CGRP described and claimed herein can ameliorate insulin resistance in muscle. Other competitive antagonists include cross-linked amylin agonists (including amylin, CGRP and active subpeptides thereof) and synthetic amylin. Direct blockage of the amylin receptor can also be accomplished with monoclonal antibodies and anti-idiotype antibodies. Other chemical antagonists to amylin and amylin agonists include organic compounds which can be assayed and/or screened for anti-amylin effects by methods disclosed herein. Noncompetitive amylin antagonists include antibodies directed to the active sites of amylin and CGRP.

DETAILED DESCRIPTION OF THE INVENTION

Amyloid is the name given to extracellular deposits of twisted-helical, paired protein filaments formed from anti-parallel beta-pleated sheets of identical polypeptide subunits See Glenner G. G., *Amyloid deposits and amyloidosis; The beta-fibrilloses.* N Engl J Med 1980; 302:1283–1292. A deposit of amyloid material, islet amyloid, is frequently found in the pancreases of patients with Type 2 diabetes mellitus. See Clark A. Cooper G. J. S. et al., *Islet amyloid formed from Diabetes-Associated Peptide may be pathogenic in Type II diabetes.* Lancet 1987; 2:231–234. In Type 2 diabetics, some workers have reported deposits of islet amyloid in more than 90 percent of the islets of Langerhans, bodies comprising clusters of endocrine-secreting cells scattered throughout the substance of the pancreas. These deposits can occupy up to four-fifths of the islet and are associated with a loss of B-cells and B-cell density. See Westermark P. Wilander W., Diabetologia 1970; 15:417–421.

Studies have indicated that the number of islets affected and the extent of amyloid deposition increases with the degree of hyperglycemia in humans (see Schneider H. M., Storkel S. Will H. M., *Das amyloid der Langerhansschen insulin und selne bezlehung zum diabetes mellitus.* Dt Med Wschr 1980; 105:1143–1147) and in Type 2 diabetic Macaca nigra monkeys. See Howard C. F., *Longitudinal studies on the development of diabetes in individual Macaca nigra.* Diabetologia 1986; 20:301–306. It has also been shown that the amount of islet amyloid in humans increases as does the severity of Type 2 diabetes, as judged by the need for insulin therapy, such that 100 percent of a series of insulin-treated Type 2 diabetics had significant islet amyloid. See Maloy et al., The relation of islet amyloid to the *clinical type of diabetes.* Human. Pathol. 1981; 12:917–922. The prevalence of islet amyloid in the Type 1 diabetic population is much the same as that in the non-diabetic population. See Maloy et al., supra. This has lead to the hypothesis that islet amyloid itself might be a factor leading to the abnormal insulin secretion in Type 2 diabetes. See Clark et al. Lancet 1987; 2:231–234.

Chemical analysis of islet amyloid has previously been frustrated by the insolubility and small amounts of the amyloid in the pancreas as a whole. Recently, a partial description of an impure peptide deposited in amyloid fibrils in an insulin expressing tumor of the islets of Langerhans (an "insulinoma"] was reported. See Westermark P. Wernstedt C. Wilander E. Sletten K., *A novel peptide in the calcitonin-gene-related family as an amyloid fibril protein in the endocrine pancreas.* Biochem Biophys Res Comm 1986; 140:827–831. The peptide described therein appears to be very impure (no more than about 10% pure) and, in fact, only the first nineteen residues could be identified. Subsequent studies, presumably on the same impure preparation, resulted in the identification of thirty-six out of thirty-seven residues of a peptide. The residue at position thirty-six could not be identified and it was suggested in the second report that two other residues were different from those previously reported. See Westermark P., Wernstedt C., Wilander E., Hayden D. W., O'Brien T. D. and Johnson K. H., *Amyloid fibrils in human insulinoma and Islets of Langerhans of the diabetic cat are derived from a neuropeptide-like protein also present in normal islet cells.* Proc Natl Acad Sci USA 1987; 84:3881–3885. Westermark et al. have designated the peptide "Islet Amyloid Polypeptide", or IAP, and subsequently IAPP.

More recently, Cooper et al. reported the purification and complete characterization of a peptide from amyloid masses extracted from Type 2 diabetic pancreases. The amino acid at position 36 was unequivocally identified as threonine in separate isolates of the peptide from two diabetic pancreases. See Cooper G. J. S., Willis A. C., Clark A., Turner R. C., Sim R. B., Reid K. B. M., *Purification and characterization of a peptide from the amyloid-rich pancreases of type 2 diabetic patients.* Proc Natl Acad Sci USA 1987; 84: 8628–8632. This peptide was shown to be highly pure (more than 90% pure) on the basis of the comparison between sequencer yields and the results of quantitative protein analysis on samples of purified peptide. Cooper et al. designated the peptide "Diabetes Associated Peptide", noting that it is present in extracts from diabetic subjects but absent from equivalent extracts from non-diabetic subjects. Diabetes Associated Peptide ("DAP") is the subject of United Kingdom Patent Application No. 8709871 (entitled "Peptides") filed on Apr. 27, 1987, and corresponding U.S. Applications filed Apr. 27, 1988 and Nov. 23, 1988, and the use of the peptide in isolation or in conjunction with insulin for the treatment of diabetes mellitus is the subject of United Kingdom Patent Application No. 8720115 (Entitled "Treatment of Diabetes Mellitus") filed on Aug. 26, 1987 by G. J. S. Cooper and M. S. Cameron.

DAP is characterized as a peptide having the following amino acid sequence:

```
 1                  5                      10
Lys—Cys—Asn—Thr—Ala—Thr—Cys—Ala—Thr—Gln—
 11                 15                     20
Arg—Leu—Ala—Asn—Phe—Leu—Val—His—Ser—Ser—
 21                 25                     30
Asn—Asn—Phe—Gly—Ala—Ile—Leu—Ser—Ser—Thr—
 31                 35
Asn—Val—Gly—Ser—Asn—Thr—Tyr                    [1]
```

Evidence indicates that the native molecule contains a disulfide bridge between the Cys residues shown at positions 2 and 7 in the primary-structure of DAP, is amidated at the 3' end, and is formed as a propeptide, i.e. amylin plus the N-terminal amino acid sequence comprising GSNFSHLFHVTSHQVEKR, KR being the processing signal. Our secondary structural prediction analysis of the amino acid sequence by the methods of Chou and Fasman, and of Kyte and Doolittle (see Chou, P. Y. Fasman, G. D. Annu. Rev. Blachem. 1978; 47:251–276 and Kyte, J., Doolittle, R. F. J. Mol. Biol. 1982; 157:105–132) further indicates that the middle portion of the molecule, in particular that portion lying between residues 18 and 27, is likely to be responsible for the formation of the islet amyloid masses, as this portion of the molecule is hydropathic and has a strong tendency to beta-sheet formation. We have experimentally confirmed this tendency, within the stated portion of the molecule, to form insoluble aggregates. We have also detected DAP in normal pancreatic tissue, albeit at lower concentrations.

Because DAP has been isolated from amyloid masses in the pancreas and because of its likely role as a receptor-mediated hormone, as discussed below, for the purposes of this invention, DAP will be referred to herein as "amylin". The amylin subpeptide [2], shown below, is amyloidogenic (that is, it possesses the tendency to form amyloid):

```
 18      20              25                [2]
His—Ser—Ser—Asn—Asn—Phe—Gly—Ala—Ile—Leu
```

We have further discovered that amylin is at least bifunctional and that two of the biological effects of the molecule are that (1) it causes B-cells within the islets of Langerhans (insulin producing cells) to release less insulin in the presence of amylin than they do in the absence of amylin, and (2) it causes a major reduction in both basal and insulin-stimulated glycogen synthesis in skeletal muscle, by causing the muscle cells to ignore the insulin signal.

We discovered that these activities are present in different portions of the molecule. We determined that one active site of the peptide is located in the C-terminal region occupying positions 27-37 of the peptide as indicated by the underlining of residues 27-37 in the above diagram of the complete amylin molecule [1]. This was demonstrated in Example 4 below by the inhibition of the release of insulin by pancreatic-islet B-cells after a glucose challenge following treatment of isolated islets of Langerhans with the amylin subpeptide amylin 27-37. In the same Example is shown the identical effect using the subpeptide CGRP 27-37, which we believe affects the amylin receptor as an agonist, as does whole CGRP.

We have also discovered that the N-terminal portion of amylin works to prevent the processing of glucose into glycogen, a process which is normally markedly stimulated by insulin. This was demonstrated by inhibition of activity of the skeletal muscle enzyme glycogen synthase as determined by demonstration of a reduction in the amount of incorporation of radioactively-labeled glucose into glycogen in rat soleus muscle with amylin and amylin subpeptides in Examples 1 and 2 below.

In essence, we believe that in normal concentrations amylin is part of a control system which reduces the action of insulin to increase carbohydrate uptake into skeletal muscle (and hence storage into glycogen), with the secondary effect of preventing hypoglycemia when insulin concentrations become excessive in relation to circulating glucose levels. See Cooper G. J. S., Cameron M. S. "Treatment of Diabetes Mellitus". United Kingdom Patent Application No. 8720115; Aug. 26, 1987. The biological activity of amylin is probably a newly discovered endocrine homeostatic mechanism whereby the body is able to control the distribution of carbohydrate energy (as glucose] according to minute to minute requirements.

The mechanism can best be thought of as complementary to the insulin-mediated control of glucose storage as glycogen in skeletal muscle. It appears likely that amylin works via a receptor-mediated mechanism which serves to control the activity of glycogen synthase, probably in a way analogous to the functioning of the insulin receptor through secondary intracellular messenger molecules (see Czech M. P., *The nature and regulation of the insulin receptor structure and function*. Ann Rev Physiol 1985; 47:357–381 and Espinal J., *Mechanisms or insulin action*. Nature 1987; 328:574–575) and thereby controls the incorporation of glucose into glycogen.

Thus, utilizing in vitro methods we found that isolated rat skeletal muscle tissue presented with insulin and radioactive glucose showed a decrease in glycogen synthesis at all physiological concentrations in the presence of amylin, and certain amylin subpeptides, compared with control experiments in which those amylin compounds were not present. These unexpected findings were confirmed as described in Examples 1 and 2, infra, with:

1) whole synthetic amylin (residues 1–37, synthesized chemically by the method of Barany and Merrifield (1979). "Solid phase synthesis" in Grass, E. Melenhater, J. eds. *The Peptides*. Academic Press New York, New York);

2) whole native amylin extracted from a diabetic human pancreas and purified according to the method of Cooper G. J. S. et al. See Cooper G. J. S., Willis A. C. et al. Proc. Natl Acad Sci USA, supra, in which the identity of the molecule was determined by amino acid sequencing according to the Edman method on an Applied Biosystems 470A protein sequencer (see Herrick, C. M., Hunkapiller, M. W. Dreyer, W. J. J. Biol. Chem. 1981; 256:7990–7997) using the O2CPTH cycle in the Version 2.0 software (Applied Biosystems, Foster City, Calif.); and 3) with various subpeptides (identified as subpeptides [3]-[5] below) corresponding to that portion of amylin comprising the first 16 residues (with and without the 2-7 disulfide bridge), and residues 8-37, all chemically synthesized according to the method of Barany and Merrifield, supra.

Subpeptides [3] and [4] in which activity in reducing the incorporation of radioactive glucose into glycogen was demonstrated were as follows:

```
 1                  5                      10        [3]
Lys—Cys—Asn—Thr—Ala—Thr—Cys—Ala—Thr—Gln
 11                 15
Arg—Leu—Ala—Asn—Phe—Leu
```

```
 1                  5                      10        [4]
Lys—Cys—Asn—Thr—Ala—Thr—Cys—Ala—Thr—Gln—
 11                 15
Arg—Leu—Ala—Asn—Phe—Leu
```

The subpeptide [5], corresponding to the 8th to the 37th residues of amylin, also reduced the incorporation of radioactive glucose into glycogen, and is shown below:

```
              10                    15                    20        [5]
Ala—Thr—Gln—Arg—Leu—Ala—Asn—Phe—Leu—Val—His—Ser—Ser 25                    30
Asn—Asn—Phe—Gly—Ala—Ile—Leu—Ser—Ser—Thr—

35
Asn—Val—Gly—Ser—Asn—Thr—Tyr
```

Amylin peptides in which no activity in reducing the insulin-stimulated incorporation of radioactive glucose into glycogen in isolated rat skeletal muscle in vitro included the following subpeptides [6] and [7], i.e., amylin 27-37, and ser$^2$, ser$^7$ amylin 1-16:

```
27           30              35              [6]
Leu—Ser—Ser—Thr—Asn—Val—Gly—Ser—Asn—Thr—Tyr 1            5               10              [7]
Lys—Ser—Asn—Thr—Ala—Thr—Ser—Ala—Thr—Gln—

11           15
Arg—Leu—Ala—Asn—Phe—Leu
```

In subpeptide [7], the SH-group containing Cys residues at positions 2 and 7 were replaced by hydroxyl group-containing Ser residues.

The results with subpeptides [3]-[7] indicated that the presence of the Cys residues in positions 2 and 7 is necessary for activity in the molecule, and that there is residual activity present in the absence of an intact Cys(2)-Cys(7) disulfide bond.

We further demonstrated, as shown in Example 4 below, that the subpeptides amylin 27-37 and CGRP 27-37 can act to reduce the amount of insulin produced by the islets of Langerhans in response to a standard glucose challenge.

Significantly, the amylin peptide itself can be used to prepare compounds that tend to neutralize or impede its activity, for example, by deamidation or the use of proamylin and, thus, to treat Type 2 diabetics. One approach relates to identification of the active site or sites of the amylin molecule, followed by the alteration of those active sites of the amylin peptide sequence, by substitution of amino acids within the active site by other amino acids, so that the peptide does not lose its binding affinity for the receptor site, but upon binding is unable to promote activity, and thereby blocks the effect of amylin. This approach can be applied to the C-terminal active sites of amylin and CGRP, namely amylin 27-37 and CGRP 27-37, and has already been demonstrated with the N-terminal active site of amylin, that portion of the molecule which is active in inducing an inhibition of the rates of basal and insulin-stimulated glycogen synthesis in muscle. Thus, we have shown in Example 3 below that the substituted subpeptide ser$^2$, ser$^7$ amylin 1-16, subpeptide [6] above, ameliorates the amylin effect in muscle. Other substituted antagonists include ser$^2$, ser$^7$ amylin, ser$^2$, ser$^7$ CGRP and ser$^2$, ser$^7$ CGRP 1-16. Substitution of chemically altered amino acid residues within the active regions of the peptides or subpeptides will also accomplish the objective of maintaining binding affinity without resulting activity. The incorporation of chemically altered residues into the amylin or CGRP active sites can be accomplished by incorporating chemically altered, activated residues into the synthetic protocol described herein. Target residues for substitution include those at amino acid position 2-7, 9, 11-13, 15, 16, 30-34 and 37.

Crystalographic analysis of the structure of amylin, and of amylin co-crystallized with its receptor, or part of its receptor, will allow analysis of the interactions between amylin and its receptor. Such analysis will allow the determination of those residues which are of primary importance in the interaction between amylin and its receptor, and will in turn indicate which residues should be changed in order to produce an effective antagonist. The structural analysis of the amylin-amylin receptor interaction will also allow the determination of the likely molecular shape and other structural features necessary in an organic inhibitor. See. e.g., Bjorkman P. J., Saper M. A., Samreoui, Bennett W. S., Strominger J. L., Wiley D. C., *Structure of the human class I histocompatibility antigen, HLA-A2.* Nature 1987; 439: 506–512. See also Bjorkman P. J., Saper M. A., Samraoui B., Bennett W. S., Strominger J. L., Wiley D. C., *The foreign antigen binding site and T cell recognition regions of class I histocompatibility antigens.* Nature 1987; 329:512–518.

The metabolic control of the production of amylin from the islets of Langerhans can be determined as follows. Using the experimental protocols outlined in Example 1 below, and using a standard radioimmunoassay or immunometric assay developed for the measurement of amylin in biological fluids (see Yalow R. S., Berson S. A., J Clin Invest 1960; 39:1157), it will be possible to determine the metabolic variables which control the synthesis and release of amylin. So, for example, isolated islets can be incubated bated with a variety of concentrations of candidate molecules, both intermediary metabolites and signal molecules such as biologically active peptides, to determine which molecules exert a positive, and which a negative, effect on the synthesis and release of amylin. The response of the islets to the various signals can be determined by measurement of the synthesis and release of amylin into the medium in which the islets are incubated, and also by determining the rate of synthesis of amylin specific mRNA. One can then examine the effect of blocking molecules on this mechanism using the same techniques as outlined below for the amylin receptor itself.

Identification of the amylin receptor site will make it possible to provide for the direct blockage of its activity. In one embodiment of the invention, monoclonal antibodies which block insulin resistance are obtained by one of two methods. Using known techniques, following identification and, if desired, purification of the amylin receptor site, monoclonal antibodies against the receptor are raised. See, e.g., Roth R. A., Cassell D. J., Wong K. Y., Maddux B., Goldfine I. D., *Monoclonal antibodies to the human insulin receptor block insulin binding and inhibit insulin action.* Proc Natl Acad Sci USA 1982; 79:7312–7316.

Antibodies to the amylin receptor can be raised in BALB/c or other similar strains of mice by immunization with purified or partially purified preparations of amylin receptor, or with cells with a high concentration of amylin receptors. The spleens of these mice can be removed, and their lymphocytes fused to a mouse myeloma cell line. After screening of hybrids by known techniques, a stable hybrid will be isolated that produces antibodies against the amylin receptor. Such activity can be demonstrated by the ability of the antibody to prevent the binding of radiolabelled amylin (e.g., $^{125}$I-labelled amylin) to it receptor. The monoclonal antibody can then be examined for its ability to prevent the actions of amylin with respect to inhibition of glucose-induced insulin secretion in isolated islets and production of insulin resistance in skeletal muscle, as described in the examples below. More specifically, analysis of the monoclonal antibodies for prevention of the insulin resistance or insulin-release inhibitory actions of amylin can be performed utilizing the screening tests as outlined in Examples 1 and 2 below, substituting the monoclonal antibody for the substituted peptide in the experimental design as in Example 4 below.

A further approach involves the use of anti-idiotype antibodies. Anti-idiotype antibodies are raised against monoclonal antibodies directed against amylin such that the anti-idiotype will have complimentary binding affinity for the amylin receptor site without, of course, the activity promotion associated with amylin binding. Utilization of anti-idiotype antibodies for blocking viral binding to cells is known in the art. See Kaufmann R. S., Noseworthy J. H., Nepom J. T., Finderg R., Fields B. N., Greene M. I., *Cell receptors for the mammalian reovirus. Monoclonal anti-idiotypic antibody blocks viral binding to cells.* J Immunol 1983; 131:2539–2541. See also Burdette S. Schwartz R. S. *Current concepts: Immunology-idiotypes and idiotypic networks.* Med Int 1987; 317: 219–224.

Amylin activity can also be prevented by utilization of techniques involving bifunctional cross-linking agents. This technique allows for binding of the receptor by cross-linked amylin and/or amylin agonists with an agent so that amylin activity is prevented. By cross-linking such a labelled agent to, for example, amylin, CGRP, or biologically active subpeptides of either of them, using known techniques (see, e.g., Galardy et al., *Photoaffinity labelling of peptide hormone binding sites.* J Biol Chem 1974; 249:3510–3518 and Yip C. C., Yeung C. W., Moule M. L., *Photoaffinity labelling of insulin receptor proteins of liver plasma membrane preparations.* Biochemistry 1980; 19:70–76 (cross-linking agent N-hydroxysuccinimide ester of p-azidobenzoic acid) they will prevent activity upon binding to the amylin receptor.

Chemical cross linkers, such as disuccinimidyl suberate, the N-hydroxysuccinimide ester of p-azidobenzoic acid, or other similar chemical compounds will be covalently bound to amylin, or subpeptides of the amylin molecule, or other amylin agonists such as CGRP, by the appropriate standard methods as reported in the literature. The derivative will then be purified by chromatography on CM-cellulose, or another appropriate stationary phase, and the purity assessed by polyacrylamide gel electrophoresis or reverse phase chromatography on C-8 or C-18 columns, with a mobile phase of 0.1% or 1% trifluoroacetic acid and an acetonitrile gradient. The cross-linked molecule is bioassayed for its ability to inhibit the insulin-inhibitory and insulinresistance producing effects of amylin, according to the experimental protocols outlined in the examples below. The crosslinked amylin will be assessed for its ability to bind to amylin receptors, for its immunoreactivity, and is labelled with $^{125}$I for example, to enable it to be used as a probe for the detection of the amylin receptor.

Another approach to the construction of suitable amylin competitive inhibitors involves biological screening for synthetic or other antagonists. Here, suitable competitive inhibitors are determined by in vitro experimentation, whereby a potential antagonist is added to isolated muscle or muscle cells and purified amylin, in the presence or absence of insulin, and glucose uptake by cells in the tissue culture are monitored. An increase in uptake in the presence of a potential antagonist will indicate the compound had the required inhibitory properties. This approach allows for relatively quick microtitre plate analysis of numbers of potential synthetic antagonists. Isolated islets of Langerhans or isolated islet B cells can also be used in a similar protocol in which increased insulin output is monitored instead.

Additionally, immunoassay screening can also be utilized, whereby synthetic or other antagonists which displace amylin or anti-idiotype antibodies from monoclonal antibodies immobilized in microtiter wells will demonstrate that such antagonists should be evaluated under the biological screening parameters discussed above. The compound to be tested or the amylin or anti-idiotype antibodies may be labelled. Immunoassay screening can be utilized as a first phase screening technique for a variety of potential antagonists. These screening methods can include the use of one or more positive and/or negative controls.

The following Examples are set forth to assist in understanding the invention and should not, of course, be construed as specifically limiting the invention described and claimed herein. Such variations of the inventions which would be within the purview of those in the art, including the substitution of all equivalents now known or later developed, are to be considered to fall within the scope of the invention as hereinafter claimed.

EXAMPLE 1

These experiments illustrate the fact that native amylin and synthetic, unamidated amylin both reduce the rate of glycogen synthesis in both basal and insulin stimulated modes. The initial experiments were performed with amylin-peptide 1-37 which was synthesized according to the method of Baray and Merrifield, as outlined above, in which the disulfide bridge between Cys(2) and Cys(7) had been reformed.

After having been starved overnight, rats were sacrificed and soleus muscles strips were prepared as previously described. See Crettaz M., Prentki M., Zaninetti D., Jean-renaud B., *Insulin resistance in soleus muscle from obese Zucker rats.* Biochem J 1980; 186:525–534 and Espinal J., Dohm L., Newsholme E. A., *Sensitivity to insulin of glycolysis and glycogen synthesis of isolated soleus muscle strips from sedentary, exercised and exercise-trained rats.* Biochem J 1983; 212:453–458.

The isolated muscles were transferred immediately into siliconized 25 ml Erlenmeyer flasks containing Krebs-Ringer bicarbonate buffer at 37° C. with the following composition (in mM); NaCl (104), Hepes (6.7), NaHCO$_3$ (22), KCl (4), CaCl$_2$ (1.1), KH$_2$, PO$_4$ (1), MgSO$_4$ (1), pyruvate (5), succinate (5), 1-glutamate (5), d-glucose (5.5). Defatted bovine serum albumin (See Chen R., *Removal of fatty acids from serum albumin by charcoal treatment.* J Biol Chem 1967; 242: 173–181) was added to a final concentration of 1.5% and the pH was adjusted to 7.31. The medium was gassed with O$_2$/CO$_2$ (95/5) during preparation; flasks were gassed with O$_2$/CO$_2$ continuously during the incubation. After 30 minutes pre-incubation the muscles were transferred into other flasks with identical Krebs-Ringer bicarbonate buffer with pyruvate, succinate or 1-glutamate, containing UDP-$^{14}$C-glucose (0.5 μCi/ml) and various concentrations of insulin (1, 10, 100 and 100 mU/L). Amylin was added to half the experiments to give a final concentration of 120 nmol/L. After 60 minutes incubation the muscles were quickly removed, blotted and freeze-clamped in liquid N$_2$ and processed for determination of the extent of UDP-$^{14}$C-glucose incorporation into glycogen. See Guendet Q., Loten E., Jenrenaud B., Renold A., *Decreased basal non-insulin stimulated glucose uptake and metabolism by skeletal soleus muscle isolated from obese-hyperglycasmic mice.* J. Clin. Invest. 1979; 58:1078–1088. The effects of insulin on glucose transport were determined by measurement of rates of conversion of glucose to lactate. See Leighton B., Challis R. A. J., Lozeman F. J., Newsholme E. A., *Effects of dexamethasone on insulin-stimulated rates of glycolysis and glycogen synthesis in isolated incubated skeletal muscles of the rat.* Biochem J 1987; 246:551–554 and Engel P., Jones J., *Causes and elimination of erratic blanks in enzymatic metabolite assays involving the use of NAD+ in alkaline hydrazine buffers.* Anal Biochem 1978; 88:475–484.

The results are set out in the accompanying TABLE 1, showing the rate of glycogen synthesis (measured as the rate of incorporation of $^{14}$C-UDP-glucose into glycogen) against insulin concentration in the presence and absence of amylin. The experiments were performed in the presence of 120 nanomoles per liter of amylin. Each result at 1 and 100 microunits per mL of insulin concentration is the mean of 11 replicate experiments. Each result at 10 and 1000 microunits per mL is the mean of 5 replicates.

The results demonstrate that at all physiological concentrations of insulin (from 1 to 100 microunits per mL), glycogen synthesis is slowed in the presence of amylin. The differences are statistically significant (p is less than 0.05 at 1 and 100 microunits per mL by the Mann-Whitney U test).

TABLE 1

Dose Response: Amylin vs. Glycogen Synthesis Inhibition
EFFECT OF SYNTHETIC AMYLIN AT VARIOUS
INSULIN CONCENTRATIONS
(Constant Amylin Concentration: 120 nmol/L)
GLYCOGEN SYNTHESIS
(μmol/h/g)*

| INSULIN CONCEN-TRATION (μU/ml) | Repl. | CONTROL ONLY Mean | Error | AMYLIN ADDED Mean | Error | RELATIVE GLYCOGEN SYNTHESIS INHIBITION |
|---|---|---|---|---|---|---|
| 1 | 11 | 2.09 | 0.18 | 1.54 | 0.18 | 26% |
| 10 | 5 | 2.25 | 0.52 | 1.72 | 0.21 | 24% |
| 100 | 11 | 5.32 | 0.26 | 4.33 | 0.28 | 19% |
| 1000 | 5 | 4.10 | 0.72 | 4.50 | 0.36 | — |

*micromoles glucosyl units per hour gram wet muscle tissue. RELATIVE GLYCOGEN SYNTHESIS INHIBITION equals the percentage by which glycogen synthesis is reduced from control. STANDARD ERROR of the mean is defined as the standard deviation divided by the square root of the number of replicates.

It will be observed that the inhibition of glycogen synthesis by amylin persists at low, and presumably even zero, insulin concentrations. Amylin therefore has its own action, which is contrary to that of insulin but probably not mediated by direct antagonism of insulin action. In support of this, we have observed that amylin is not capable of significantly displacing insulin from its receptor on red blood cells. This evidences the existence of a receptor for the peptide amylin in the skeletal muscle cells of the rat. Of course, this experiment was performed with amylin synthesized according to the human sequence and it is likely, although as yet unknown, that the sequence of "rat-amylin" is distinct from that of human amylin. Therefore, it is also likely that the effect of rat amylin in this system could be significantly greater than that of human amylin.

Isolated native amylin also has the biological effect of inhibiting the rates of basal and insulin-stimulated glycogen synthesis in skeletal muscle, as the following experiments demonstrate. Experiments were performed with human amylin, isolated and characterized from the pancreas of a human Type 2 diabetic according to the method of Cooper G. J. S. et al., Proc Natl Acad Sci 1987; 84:8628–8632. Samples used were from the broad peak area of the final isolation step of HPLC reverse phase chromatography with a mobile phase of 1.0 percent trifluoroacetic acid, with gradient elution by acetonitrile from 5 to 80 percent over 45 minutes, on a C-18 column with detection of peptides by ultraviolet spectrophotometry at 280 nm. The exact concentration of amylin was confirmed by quantitative amino acid analysis and by the yield on amino acid sequencing. A graph can be constructed showing the elution profile of amylin, with the Yaxis representing an $AUFS_{280}$ of 0.02 or 0.05 absorbance units (AUFS; absorbance units, full scale deflection) and the X-axis the percentage acetonitrile in the gradient. Amylin eluted at an acetonitrile percentage of 67.9 percent.

The experiments were performed in the manner indicated in Example 4 below, except that amylin isolated from a human diabetic pancreas was used in place of material synthesized chemically. Samples indicated as "amylin" contained native amylin at the stated concentrations, as well as insulin at a basal concentration of 10 μU/mL (TABLE 2), or at the stimulatory level of 100 μU/mL (TABLE 3). These results are presented below in TABLES 2 and 3, where n represents the number of replicates in each group. The rates of glycolysis, as indicated by the rates of lactate synthesis, were not significantly different between groups. Statistical analysis was performed by the t-test, and significance was assessed as the difference between an amylin treated sample and the appropriate insulin-treated control.

TABLE 2

Glycogen Synthesis Inhibition in Rat Muscle Cells
EFFECT OF NATURAL WHOLE AMYLIN AT
BASAL INSULIN CONCENTRATION
(Insulin Concentration: 10 μU/ml)

| | AMYLIN CONCNTRTN (nmol/L) | Repl. | GLYCOGEN SYNTHESIS (μmol/h/g)* Mean Value | Std Error | RELATIVE INSULIN RESISTANCE |
|---|---|---|---|---|---|
| None (Control) | — | 4 | 1.43 | 0.10 | 0% |
| Amylin, Fraction 2 | 0.4 | 4 | 1.12 | 0.06 | 22% |
| Amylin, Fraction 3 | 0.4 | 3 | 1.11 | 0.06 | 22% |
| Average | | | 1.12 | 0.06 | 22% |
| Amylin, Fraction 2 | 2.0 | 4 | 0.82 | 0.12 | 43% |
| Amylin, Fraction 3 | 2.0 | 4 | 0.62 | 0.11 | 57% |
| Average | | | 0.72 | 0.12 | 50% |

*micromoles glycosyl units per hour per gram wet muscle tissue. RELATIVE GLYCOGEN SYNTHESIS INHIBITION equals the percentage by which glycogen synthesis is reduced from control. STANDARD ERROR of the mean is defined at the standard deviation divided by the square root of the number of replicates. All measurements of glycogen synthesis were determined by the T-test to be significantly different from the control value with p < 0.025 in all cases.

TABLE 3

Glycogen Synthesis Inhibition in Rat Muscle Cells
EFFECT OF NATURAL WHOLE AMYLIN AT
STIMULATORY INSULIN CONCENTRATION
(Insulin Concentration: 100 µU/ml)

| AMYLIN CONCNTRTN (nmol/L) | Repl. | GLYCOGEN SYNTHESIS (µmol/h/g)* Mean Value | Std Error | RELATIVE INSULIN RESISTANCE |
|---|---|---|---|---|
| Experiment #1 | | | | |
| None (Control) | — | 3 | 2.83 | 0.10 | 0% |
| Amylin, Fraction 2 | 0.4 | 4 | 2.00 | 0.29 | 29% |
| Experiment #2 | | | | |
| None (Control) | — | 4 | 3.69 | 0.57 | 0% |
| Amylin, Fraction 2 | 2.0 | 5 | 1.97 | 0.45 | 47% |

*See Table 2 for explanation.

It can be seen that concentrations of extracted amylin as low as 0.4 nmol/L are effective in significantly reducing the rate of both basal and insulin stimulated glycogen synthesis in isolated rat muscle, and that an amylin concentration of 2.0 nmol/L reduces the basal rate of glycogen synthesis by 50 percent, and the insulin-stimulated rate by 47 percent. This must be contrasted with the results of the previous experiment performed in an identical manner but with chemically synthesized amylin, in which a concentration of unamidated synthetic amylin of 120 nmol/L was required to produce a significant reduction in glycogen synthesis.

These results demonstrate that amylin extracted from a natural source was more potent than amylin that was chemically synthesized as described, by at least a factor of 120/2, or 60 fold. This indicates that there is a feature of the isolated molecule that is not completely reproduced by synthesized material. This may be because the reformation of the Cys(2)-Cys(7) disulfide bridge is incomplete in the synthetic molecule.

EXAMPLE 2

Experiments with synthetic subpeptides of amylin were also performed, the individual structures of which have already been indicated in the text of the application, as subpeptides [3]-[5]. Amylin subpeptides used in experiments accomplished by the above methods to localize of the glycogen-synthesisinhibitory active site of amylin included: [3] Amylin 1-16, with the Cys(2)-Cys(7) bridge reformed; [4] Amylin 1-16, reduced; [5] Amylin 8-37; [6] Amylin 27-37; and [7] Amylin 1-16 with Ser residues substituted for the Cys residues 2 and 7.

All peptides were synthesized on an Applied Biosystems 430A Peptide Synthesizer, using commercially available Pam resins and t-butyloxycarbonyl protected amino acids and reagents, with cleavage of the peptide from the resin and the side-chain protecting groups simultaneously by anhydrous hydrofluoric acid treatment with anisole as a free radical trap, followed by extraction of side-chain protecting groups with ether, dissolution of the peptide in 15 percent acetic acid, filtration from resin and purification by HPLC on a C-8 reverse phase column (Aquapore RP-3000, Brownlee Laboratories, Santa Clara, Calif.) with a mobile phase of 0.1% aqueous trifluoro-acetic acid on an acetonitrile gradient and detection of peptides by ultraviolet spectrophotometry at 206 nm. The disulfide bridge linking the cysteine residues at positions 2 and 7 of peptide [3] was reformed by the following method. After synthesis, the peptide was dissolved in dilute solution in water at pH 8.0 for 12 hours, and was then recovered by lyophilization and repurified on a High Performance Liquid Chromatography (HPLC) system by reverse phase chromatography in an acetonitrile—aqueous 0.1% trifluoroacetic acid system with detection of peptides by ultraviolet absorbance at 206 nm. See, e.g., Cooper G. J. S. et al., Proc. Natl Acad. Sci. USA 1987; 84:8626-8632. The disulfide bond of peptide [4] was retained in a reduced form by reduction with dithiothreitol after the de-blocking procedure following synthesis.

The results indicated that significant activity was present in the subpeptides [3], [4] and [5], i.e., amylin 1-16 with Cys(2)-Cys (7) reformed by oxidation, amylin 1-16 reduced, and amylin 8-37 (data not shown). Activity was absent from the subpeptides [6] and [7], i.e., from amylin 27-37 and amylin 1-16 with serine residues substituted for cysteine residues. Accordingly, the activity of amylin in inhibiting the rates of both basal and insulin-stimulated glycogen synthesis in skeletal muscle are dependent on certain features of the amylin molecule:

1. The presence of the cys residues at positions 2 and 7 in the molecule;
2. Other portions of the sequence between residues 7 and 16.

EXAMPLE 3

Experiments using amylin 1-16 with serines substituted for cysteines at positions 2 and 7 ($ser^2$, $ser^7$ amylin 1-16) as an amylin blocker were performed as described in Example 2. We utilized an artificially synthesized peptide amylin 1-16, with serines substituted for cysteines and extracted human amylin. Experiments were performed with amylin concentrations of both 2.0 and 0.2 nmol/L, a stimulatory insulin concentration of 100 uU/mL, and with the $ser^2$, $ser^7$ amylin 1-16 at a concentration of $10^{-5}$ mol/L. The results obtained in these experiments are included in the following TABLE 4.

TABLE 4

Amylin Antagonist Reduction of Glycogen Synthesis Inhibition
EFFECT OF MODIFIED AMYLIN SUBPEPTIDE $SER^2$, $SER^7$
AMYLIN 1-16 IN RAT MUSCLE CELLS
(Stimulatory Insulin Concentration: 100 µU/ml)

| CONCENTRATION (nmol/L) AMYLIN | ANTG | Repl. | GLYCOGEN SYNTHESIS (µmol/h/g)* Mean Value | Std Error | Rltv Insulin Resist | Rltv Antg Effect |
|---|---|---|---|---|---|---|
| Experiment #1 | | | | | | |
| None (Control) | 0.0 | 0 | 3 | 2.83 | 0.10 | 0% | — |
| Amylin alone | 0.2 | 0 | 4 | 2.00 | 0.29 | 29% | 0% |
| Amylin & Antgnst | 0.2 | 10,000 | 3 | 2.22 | 0.72 | 22% | 24% |
| Experiment #2 | | | | | | |
| None (Control) | 0.0 | 0 | 4 | 3.69 | 0.57 | | 0% |

TABLE 4-continued

Amylin Antagonist Reduction of Glycogen Synthesis Inhibition
EFFECT OF MODIFIED AMYLIN SUBPEPTIDE $SER^2$, $SER^7$
AMYLIN 1-16 IN RAT MUSCLE CELLS
(Stimulatory Insulin Concentration: 100 μU/ml)

| | CONCEN-TRATION (nmol/L) | | | GLYCOGEN SYNTHESIS (μmol/h/g)* | | Rltv Insulin Resist | Rltv Antg Effect |
|---|---|---|---|---|---|---|---|
| | AMYLIN | ANTG | Repl. | Mean Value | Std. Error | | |
| Amylin alone | 2.0 | 0 | 3 | 1.97 | 0.45 | 47% | 0% |
| Amylin & Antgnst | 2.0 | 10,000 | 3 | 2.63 | 0.29 | 20% | 38% |

*micromoles glycosyl units per hour per gram wet muscle tissue. RELATIVE GLYCOGEN SYNTHESIS INHIBITION equals the percentage by which glycogen synthesis is reduced from control. RELATIVE ANTAGONIST EFFECT equals the percentage by which relative insulin resistance is reduced from amylin alone. STANDARD ERROR of the mean is defined as the standard deviation divided by the square root of the number of replicates.

These results demonstrate that the amylin used at concentrations of both 2.0 nmol/L and 0.2 nmol/L was active in the inhibition of glycogen synthesis, with a significant decrease over controls in both experiments. On the other hand, after the addition of $ser^2$, $ser^7$ amylin 1-16 there was no significant difference between the insulin stimulated rates of glycogen synthesis, and that in the samples with insulin, amylin and $ser^2$, $ser^7$ amylin 1-16 treated muscle. Although the inhibitory effect of the $ser^2$, $ser^7$ amylin 1-16 is incomplete, it can clearly be seen that the rate of glycogen synthesis moved back toward the uninhibited rate in both experiments at the two concentrations of amylin (2.0 and 0.2 nmol/L).

Thus, a competitive inhibitor of the action of amylin, in this case $ser^2$, $ser^7$ amylin 1-16 (of the type in which different amino acids are substituted for important residues within the active site of a peptide), is capable of partially ameliorating the insulin resistance produced by amylin alone. Additionally, the substituted peptide $ser^2$, $ser^7$ amylin 1-16 is an inhibitor, we believe a competitive inhibitor, of the effect of amylin to inhibit the rate of insulin-stimulated glycogen synthesis in isolated skeletal muscle.

EXAMPLE 4

The following experiments illustrate the fact that subpeptides of amylin can act to reduce the amount of insulin produced by isolated islets of Langerhans in response to a standard glucose challenge. Similar results have been obtained using whole amylin. All experiments were performed by known methods used in experimental practice. See. e.g., Lacey P. E., and Kostianovsky M., *Method for the isolation of intact islets of Langerhans from the rat pancreas*. Diabetes 1967; 16:35–39.

Briefly, rats were killed, and islets of Langerhans were isolated from their pancreases. Experiments were performed either with freshly isolated islets or after overnight incubation of islets (23 h) in standard culture medium and conditions at 37° C. Synthetic amylin peptide 27-37 or synthetic calcitoningene related peptide (CGRP) was dissolved in a 1.0 mmol/L citric acid/sodium citrate buffer, pH 3.0, and the concentration of the amylin 27-37 was verified by quantitative amino acid analysis. See, e.g., Cooper G. J. S et al., Proc Natl Acad Sci USA 1987; 84:8628–8632. Incubation of islets for these experiments was carried out in standard Krebs-Heinsleit buffer, and it was verified that the addition of the 1.0 mmol/L citrate buffer had no effect on the pH of the incubation medium. Stimulation of islets was carried out at the standard stimulatory glucose concentration of 10 mmol/L.

Production of insulin is expressed as μU/islet/h. All experiments were performed with five replicates per point. The integrity of the islet response was assessed by comparing the responses after stimulation of different aliquots of islets by two and ten mmol/L glucose, respectively, and the strength of the inhibitor response was judged against that induced by 1 μg/ml (650 nmol/L) somatostatin. Somatostatin is a 14 amino acid peptide which is a known, potent inhibitor of the insulin secretory response of islet B-cells to glucose. See Arimura A. Biomed res 1981; 2:233–257. CGRP has also been shown to be a potent inhibitor of glucose stimulated insulin secretion. See Petterson M., Ahren B., Bottcher G., Sundler F., Endocrinology 1986; 119:865–869.

The results are shown in TABLE 5 below and all results are expressed as ± standard error of the mean (s.e.m.). The significance of differences between the means of groups is assessed by the t-test. The result of stimulation by 10 mmol/L glucose is compared with the results of stimulation at 2 mmol/L glucose. In all other experimental conditions, the significance of the inhibitory effect is measured against the effect of 10 mmol/L glucose alone.

TABLE 5

INSULIN SECRETION IN RAT ISLET CELLS
Effect of Synthetic Partial Amylin and Other Hormones
(Stimulatory Glucose Level: 10 mmol/L)

| SUBSTANCE INHIBITION | Concentration (nmol/L) | Repl. | INSULIN PRODUCTION (μU/islet/hr) | | RELATIVE INSULIN SECRETION INHIBITION |
|---|---|---|---|---|---|
| | | | Mean Value | Std. Error | |
| None (Control) | — | 5 | 80 | 14 | 0% |
| Amylin 27-37 | 1000 | 5 | 65 | 17 | 19% |
| Amylin 27-37 | 100 | 5 | 48 | 9 | 40% |
| Amylin 27-37 | 10 | 5 | 45 | 7 | 44% |
| Somatostatin | 650 | 5 | 44 | 12 | 45% |
| CGRP 27-37 | 1000 | 5 | 46 | 10 | 42% |
| CGRP 27-37 | 100 | 5 | 36 | 8 | 55% |
| CGRP 27-37 | 10 | 5 | 36 | 9 | 55% |

RELATIVE INSULIN SUPPRESSION equals the percentage by which insulin production is reduced from control. "CGRP" = Calcitonin Gene Related Peptide. STANDARD ERROR of the mean is defined as the standard deviation divided by the square root of the number of replicates.

These experiments indicate that the peptide amylin 27-37 is a potent inhibitor of glucose stimulated insulin secretion from the isolated rat islet. There was no significant difference between the inhibition of insulin secretion seen with various concentrations of amylin 27-37 and that seen with somatostatin (1 ug/mL; 650 nmol/L), a known potent inhibitor of insulin secretion, or with the varying concentrations of the peptide CGRP 27-37. There was a trend for the inhibition caused by CGRP 27-37 to be slightly greater than that caused by amylin 27-37, but this never reached significance.

As an insufficient insulin response to glucose is one of the characteristic pathophysiological features of Type 2 diabetes, and as there is likely to be an excessive production of amylin in that state (as shown by the presence of large amounts of amyloid), this action of amylin may very well be diabetogenic (tending to cause diabetes).

Utilizing the information provided in Example 3 above, one or more amylin peptides with substitutions of amino acids in the sequence of amylin 27-37 can be produced as an inhibitor of the effect of amylin 27-37 in inhibiting the insulin response to a glucose stimulus. Such a substituted peptide, and other compounds with similar properties, will be of great benefit in treatment of Type 2 diabetes mellitus.

We claim:

1. A method for treating type 2 diabetes mellitus comprising administering an amylin antagonist to a subject in an amount effective to reduce amylin activity in said subject, wherein said amylin antagonist comprises an antibody directed to amylin.

2. The method of claim 1 wherein said antibody directed to amylin binds in the region of amino acids 1-16.

3. The method of claim 1 wherein said antibody directed to amylin binds in the region of amino acids 27-37.

4. The method of any of claims 1-3 wherein said antibody directed to amylin binds specifically to amylin.

5. The method of any of claims 1-3 wherein said antibody directed to amylin is monoclonal.

6. The method of claim 4 wherein said antibody directed to amylin is monoclonal.

7. A method for treating type 2 diabetes mellitus comprising administering an amylin antagonist to a subject in an amount effective to reduce amylin activity in said subject, wherein said amylin antagonist comprises an anti-idiotype antibody directed to an antibody directed to amylin.

8. The method of claim 7 wherein said anti-idiotype antibody is monoclonal.

* * * * *